(12) United States Patent
Hausmann et al.

(10) Patent No.: US 7,001,403 B2
(45) Date of Patent: Feb. 21, 2006

(54) SAW BLADE FOR MEDICAL APPLICATIONS

(76) Inventors: Thomas Hausmann, Sperberstrasse 16, 74564 Carilsheim (DE); Christian Hendrich, Sandgrubenweg 2, 97084 Wurzburg (DE)

(*) Notice: Subject to any disclaimer, the term of this patent is extended or adjusted under 35 U.S.C. 154(b) by 524 days.

(21) Appl. No.: 10/220,692

(22) PCT Filed: Mar. 5, 2001

(86) PCT No.: PCT/DE01/00822

§ 371 (c)(1),
(2), (4) Date: Sep. 5, 2002

(87) PCT Pub. No.: WO01/66123

PCT Pub. Date: Sep. 13, 2001

(65) Prior Publication Data

US 2003/0032971 A1 Feb. 13, 2003

(30) Foreign Application Priority Data

Mar. 7, 2000 (DE) .......................... 100 10 526

(51) Int. Cl.
*A61B 17/14* (2006.01)
*A61B 17/32* (2006.01)

(52) U.S. Cl. ...................... 606/178; 606/167; 606/169; 606/171; 606/176; 606/177; 30/166.3; 30/182; 125/15; 125/16.01; 125/18; 125/19

(58) Field of Classification Search ............... 606/167, 606/169, 171, 176, 177, 178; 30/166.3, 392, 30/584, 182, 267; 125/15, 16.01, 18, 19
See application file for complete search history.

(56) References Cited

U.S. PATENT DOCUMENTS

| 4,036,236 | A | | 7/1977 | Rhodes, Jr. | |
|---|---|---|---|---|---|
| 4,513,742 | A | * | 4/1985 | Arnegger | 606/178 |
| 5,122,142 | A | * | 6/1992 | Pascaloff | 606/82 |
| 5,133,728 | A | * | 7/1992 | Petersen | 606/176 |
| D361,029 | S | * | 8/1995 | Goris | D8/70 |
| 5,554,165 | A | | 9/1996 | Raitt et al. | |
| 6,656,186 | B1 | * | 12/2003 | Meckel | 606/82 |
| 6,684,481 | B1 | * | 2/2004 | Kullmer | 28/558 |

FOREIGN PATENT DOCUMENTS

| DE | 38 38 844 A | 5/1990 |
|---|---|---|
| EP | 0 695 607 A | 2/1996 |
| FR | 1 169 494 A | 12/1958 |

* cited by examiner

*Primary Examiner*—Glenn K. Dawson
*Assistant Examiner*—Michael Mendoza
(74) *Attorney, Agent, or Firm*—Nixon Peabody LLP; David S. Safran

(57) ABSTRACT

A saw blade for medical, in particular surgical, applications having a recess for mounting the saw blade inside a saw which exerts an saw movement, especially an oscillating saw movement, to the saw blade. In order to improve the dynamic behavior of the saw blade, longitudinal flat areas of a surface of the saw blade are provided with a plurality of superficial impressions of a defined contour that are aligned at an angle to the longitudinal axis of the saw blade.

21 Claims, 6 Drawing Sheets

SAW BLADE FOR MEDICAL APPLICATIONS

BACKGROUND OF THE INVENTION

1. Field of the Invention

The invention relates to a saw blade for medical, particularly surgical applications, having a receiver for accommodating a saw which applies a sawing motion, especially an oscillating sawing motion, to the saw blade.

2. Discussion of Related Art

Particularly in the area of knee surgery, is it necessary to cut the knee or knee sections and other tissue, such as cartilage or the like, by means of a saw when an artificial knee joint is implanted. To do this, compressed air-driven or electrical saws (often battery-driven devices) are known which have a saw blade as is shown in FIG. 1.

The saw blade (1) is made as a thin sheet and, therefore, has a flat structure. On one end, it has a sawtooth profile (2) which cuts the bone. The saw blade (1) is held in the saw by means of a receiver (3), for example, with a multitooth profile. The saw applies a sawing motion to the saw blade. In this case, the saw turns the saw blade back and forth by a small angle around the axis of the receiver (3), causing the sawtooth profile (2) to move in an oscillating manner. In doing so, the saw applies to the saw blade (1) such large angular movements on the receiver (3) that the lifting motion of the sawtooth profile (2) is only a few millimeters. The sawing frequency generally varies on the order of roughly 250 Hz.

Generic saw blades are known from U.S. Pat. No. 4,036,236 and EP 0695 607 A1. The saw blades described by those documents provide ribs or grooves which run linearly from the receiver 3 as far as the sawtooth profile 2 for purpose of stiffening or for reducing the weight of the saw blade.

However, when bones are being cut in the knee area what is important is making a cut as exact as possible. The required precision varies less than a millimeter, and known saw blades engender problems in this respect.

The known saw blade, during sawing, must oscillate with such a high frequency that the dynamic forces cause vibration of the saw blade in the direction normal to the flat area of the saw blade. In the resonant area, the vibration amplitude can become so large that in spite of the use of templates, which exactly guide the saw, the required sawing precision cannot be maintained. The cut becomes inexact which results in the corresponding consequences in surgery.

Another disadvantage is caused by the fact that the saw being used is exposed to high dynamic stress so that its bearings are subject to high loads and wear. In the saws which are conventionally used, it is necessary to often replace their bearings so that sufficient accuracy can be achieved.

Reducing the thickness of the saw blade does not yield any overall benefit, since the dynamic effect as a result of the reduced mass of the saw blade is less, but deflection of the blade is increased when working forces are applied.

SUMMARY OF THE INVENTION

An object of the invention is to develop a saw blade of the generic type that has much improved dynamic behavior, and, nevertheless, has high static stiffness. Thus, it would become possible to make precise cuts through bones. Furthermore, the durability of the saw will be improved, particularly with regard to its bearings.

Achieving this object by the invention is characterized in that the flat area of the saw blade has a number of surface impressions of a defined contour which are aligned relative to each other along a straight line, where the straight line is aligned at an angle to the lengthwise axis of the saw blade.

The impressions in the surface of the saw blade influence the ability of the blade to transport or relay vibrations, i.e., they influence the dynamic behavior of the saw blade. In this way, the vibration behavior of the saw blade can be greatly reduced when in operation; while the precision of the cut is increased accordingly.

Preferably, the surface impressions are located on the flat areas of both sides of the saw blade; specifically, they can be located opposite one another on the two sides of the flat area.

Influencing the dynamic behavior is affected by the impressions since the surface impressions are aligned in an oriented arrangement relative to each other along a straight line which is aligned at an angle to the lengthwise axis of the saw blade.

That angle is preferably between 15° and 45°, especially between 25° and 35°.

The surface impressions can be contoured to have different geometries. First of all, rectangular outlines are possible, preferably where the length of the side of a rectangle is at least 1.5 times, and preferably at least twice the width of the rectangle.

Alternatively, surface impressions in the form of squares, triangles, circles or polygons are possible. Here the side lengths or diameters of the surface impressions are advantageously between 1.5 mm and 30 mm, preferably between 2 mm and 10 mm.

Furthermore, dynamic properties are especially improved when the surface impressions are located at equidistant intervals to one another. The distance between two surface impressions can be between 0.5 mm and 10 mm, and preferably between 1 mm and 5 mm.

The depth of the surface impressions can be between 0.05 mm to 0.5 mm, and preferably 0.1 mm and 0.2 mm.

The saw blade according to the development can be composed of high-strength steel, such as high-alloy chromium steel which is preferred. The tensile strength of the steel should also be at least 1200 N/mm$^2$, while the surface hardness of the saw blade should be at least 60 HRC (HRC is the Rockwell hardness).

The embodiments of the saw blade of the invention leads to the vibrations during sawing being reliably damped at the start of the vibration building-up process. Thus, over the entire frequency range with which the saw blade is excited during the sawing process, the blade does not tend to vibration perpendicular to the blade surface, and the cutting precision is thus significantly increased.

BRIEF DESCRIPTION OF THE DRAWINGS

Various embodiments of the invention are shown in the drawing figures.

DETAILED DESCRIPTION OF THE INVENTION

Figure 1:
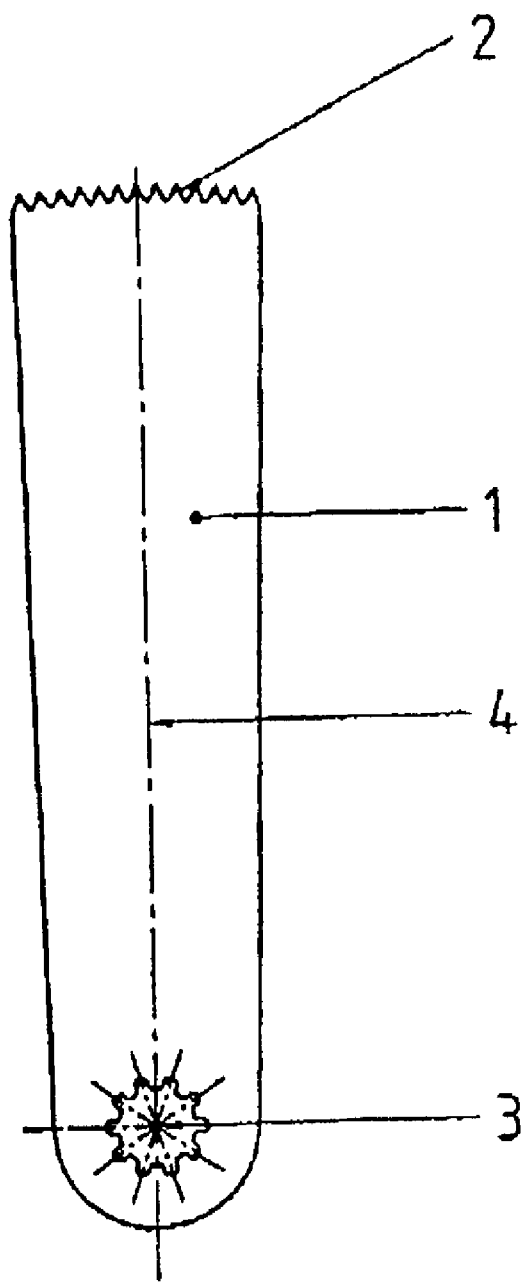
FIG. 1 schematically shows an overhead view of a known saw blade.
Figure 2:
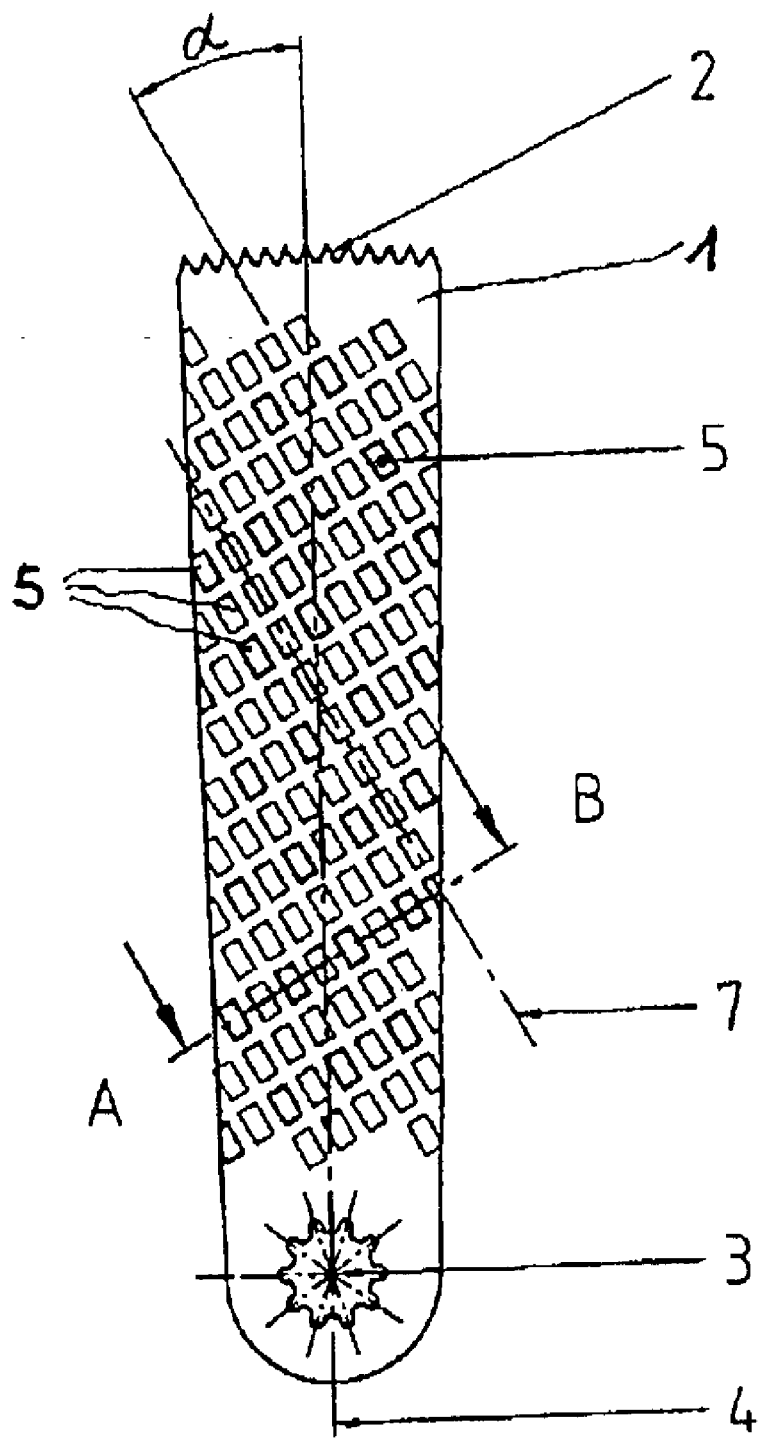
FIG. 2 shows a view of the saw blade according to a first embodiment of the invention.

The saw blade shown in FIG. 2 in an overhead view includes a flat base body of high-alloy chromium steel. The saw blade 1 has a lengthwise axis 4. On one end, the saw blade 1 is provided with a sawtooth profile 2 made for example by a laser cutting process. On the other end, a receiver 3 is machined which has a multitooth profile that interacts with a corresponding counterpiece of the saw (not shown).

In operation, the saw turns the saw blade 1 around the center point of the receiver 3 in the plane of the flat area surfaces of the blade so that the sawtooth profile 2 is moved back and forth, and thus can cut through bone and other tissue.

To improve the dynamic behavior, the surface of the saw blade is provided with a host of surface impressions 5. In the embodiment shown in FIG. 2, the impressions 5 are made in the form of small rectangles.

As can be seen in FIG. 2, the individual rectangles are oriented in a straight line alignment to one another. The rectangles are positioned a short distances behind each other along a straight line 7 shown as a broken line in FIG. 2. The line 7 in turn is located at an angle α to the lengthwise axis 4. The angle α is preferably 30°.

As already mentioned, the added elements 5 are impressions on the surface of the saw blade 1. This is apparent from FIG. 3 where the section A–B of FIG. 2 is shown. With an embossing tool (not shown) the impressions 5 have been embossed on either side of the flat areas 6, so that the respective impressions 5 are formed opposite one another on both sides of the saw blade 1 to form a compacted or compressed material area 8 which as a result of the material compression has the property of deflecting vibration-induced excitations. The special arrangement of the impressions 5 along the angularly aligned line 7 causes deflection of the vibration excitation "out of the saw blade", so that the dynamic behavior of the saw blade 1 is significantly improved.

The impressions 5 can also be made in alternate forms.

Figure 3:
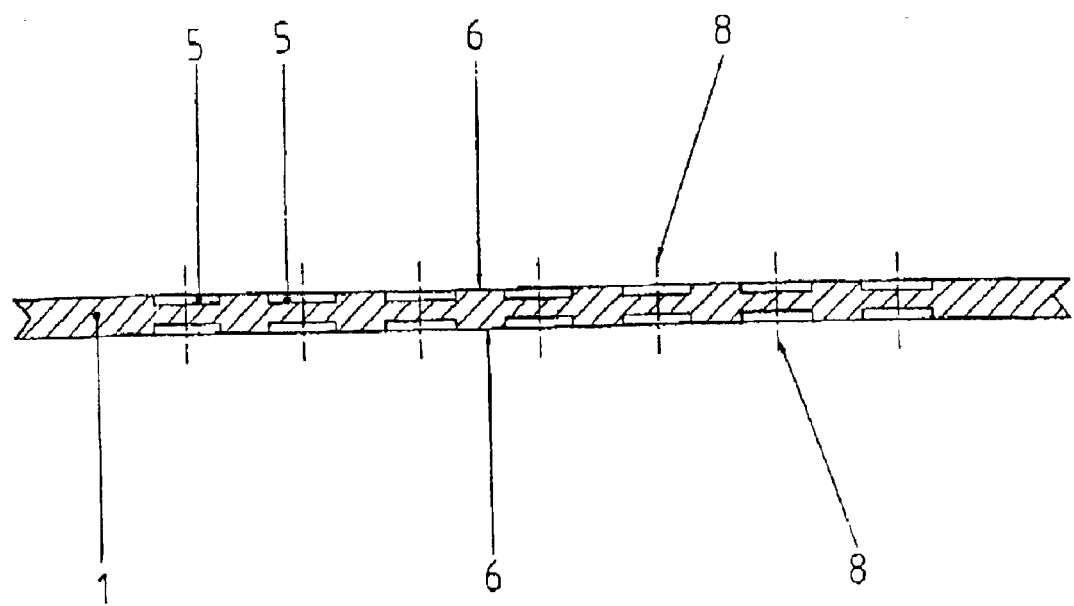
FIG. 3 shows a view of the saw blade along section A–B in FIG. 2.

Instead of the rectangular cross sectional shape in FIG. 3 there can also be trough-shaped or similar impressions which enable a continuous material transition from the flat area 6 into the impression area. In this case, the impressions 5 can be produced using a crowned embossing die.

Figure 4:
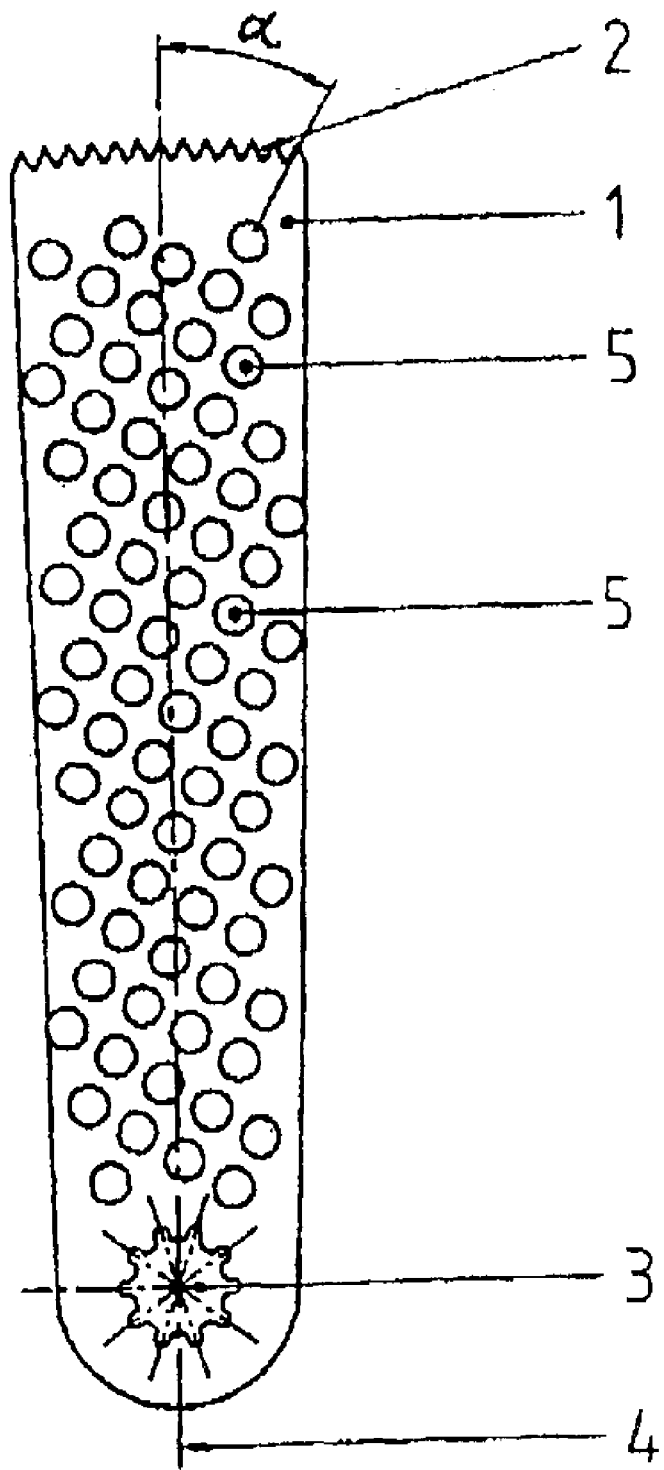
FIG. 4 shows another embodiment of the invention.

FIG. 4 shows another embodiment where the impressions 5 are made in the form of circles. The circles are again aligned along a straight line which is at an angle α to the axis 4 of the saw blade.

Figure 5:
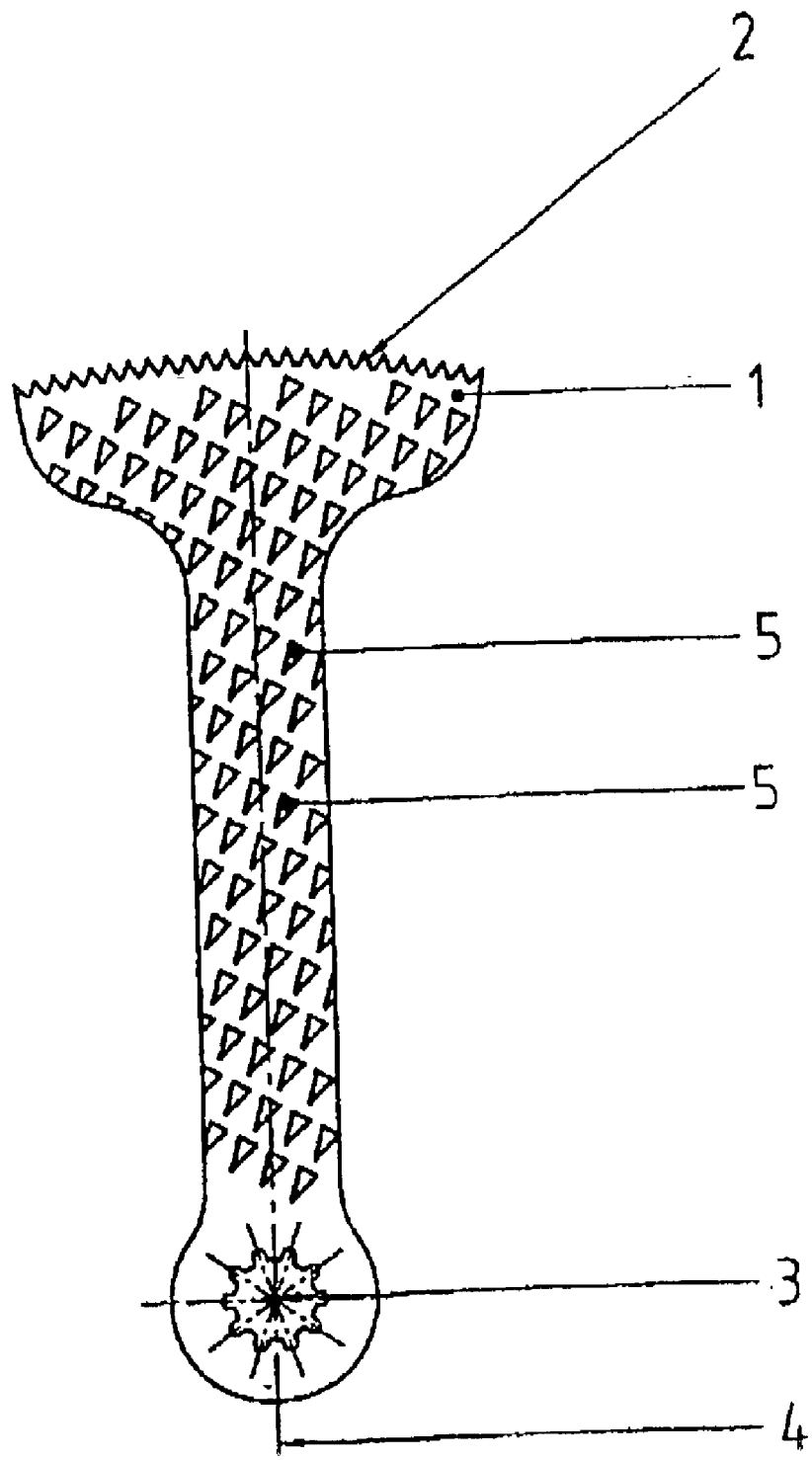
FIG. 5 shows still aother embodiment of the saw blade which includes a horizontal projection.

FIG. 5 shows that the invention can apply to other basic shapes of the saw blade 1. Here, the saw blade 1 is made in the manner of a hammerhead in the area of the sawtooth profile 2.

Figure 6:
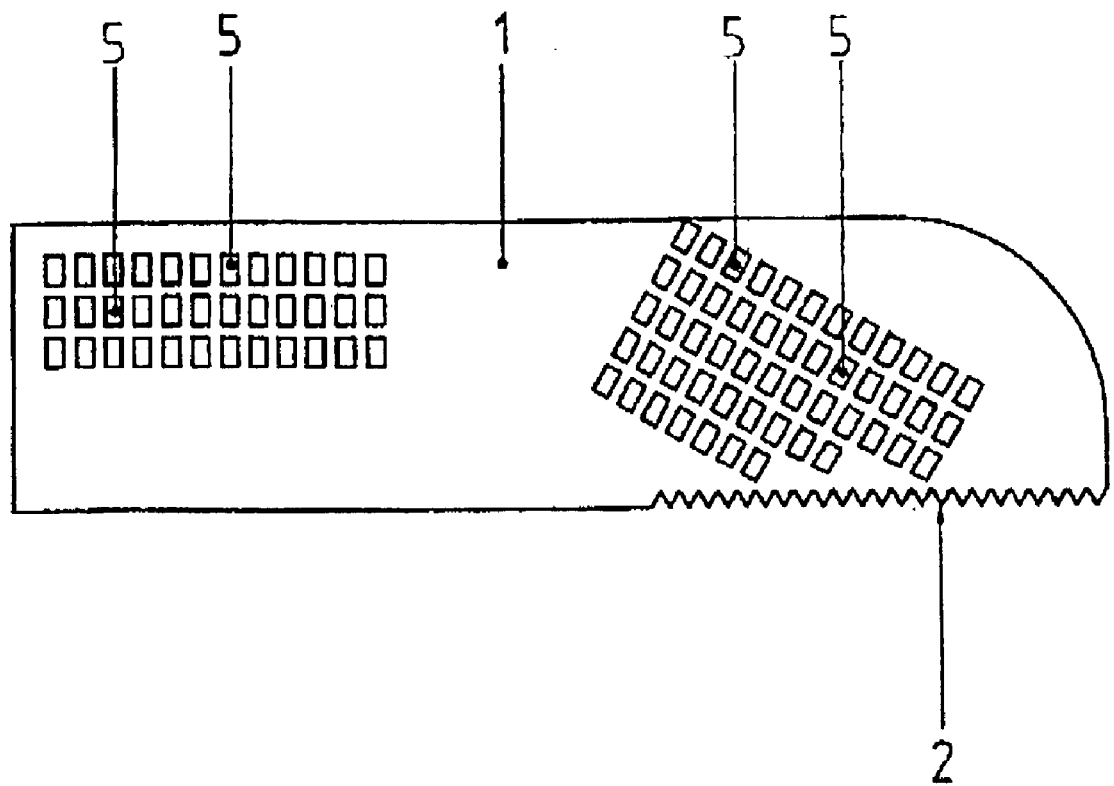
FIG. 6 finally shows still another embodiment of the invention for a sabre saw blade.

The invention can also be applied to other types of medical saws as seen in FIG. 6. The sabre saw blade 1 shown there has surface impressions 5 are both aligned with the lengthwise axis of the saw blade and at an angle α to the lengthwise axis of the saw blade, so that the vibrations, which build up, are deflected out of the saw blade 1. Here the dynamic behavior of the saw blade 1 in operation is also greatly improved.

The surface impressions 5 can be efficiently made by an embossing process so that the saw blade 1 can be economically produced.

What is claimed is:

1. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein the angle at which adjacent surface impressions are oriented relative to each other is between 15°–45°.

2. Saw blade as claimed in claim 1, wherein the surface impressions are formed on each of the opposed flat surfaces of the saw blade.

3. Saw blade as claimed in claim 2, wherein each surface impression on one flat surface of the saw blade is aligned with a surface impression on the opposed flat surface of the saw blade.

4. Saw blade as claimed in claim 1, wherein the distance between two adjacent surface impressions is between 0.5 mm–10 mm.

5. Saw blade as claimed in claim 1, wherein the depth of each surface impression is between 0.05 mm–0.5 mm.

6. Saw blade as claimed in claim 1, wherein the saw blade is composed of high strength steel.

7. Saw blade as claimed in claim 6, wherein the high strength steel is a high-alloy chromium steel.

8. Saw blade as claimed in claim 6, wherein the tensile strength of the high strength steel is at least 1200 N/mm$^2$.

9. Saw blade as claimed in claim 1, wherein the saw blade has a surface hardness of at least 60 HRC.

10. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein each of the surface impressions has a rectangular outline.

11. Saw blade as claimed in claim 10, wherein the length of a side of the rectangular surface impressions is at least 1.5 to 2.0 times the width of the rectangle.

12. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein each of the surface impressions has a square outline.

13. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein each of the surface impressions has a triangular outline.

14. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein each of the surface impressions has a circular outline.

15. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein each of the surface impressions has a polygonal outline.

16. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein a length of the sides of each surface impression is between 1.5 mm–30 mm.

17. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein the angle at which adjacent surface impressions are oriented relative to each other is between 25°–35°.

18. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein a length of the sides of each surface impression is between 2 mm–10 mm.

19. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein the diameter of each circular surface impression is between 1.5 mm–30 mm.

20. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein the distance between two adjacent surface impressions is between 1 mm–5 mm.

21. Saw blade for surgical applications which includes a receiver at one end of the saw blade for accommodating a counterpiece of a saw to enable an oscillating sawing motion to be applied to the saw blade and a sawtooth profile at an end of the saw blade opposite the receiver, comprising:

opposed flat surfaces extending along a longitudinal axis of the saw blade, wherein at least one of the opposed flat surfaces of the saw blade has a plurality of aligned surface impressions such that adjacent surface impressions are oriented relative to each other along a straight line disposed at an angle relative to the longitudinal axis of the saw blade; and wherein the depth of each surface impression is between 0.1 mm–0.2 mm.

* * * * *